US00PP10319P

United States Patent [19]

Whitcomb

[11] Patent Number: Plant 10,319

[45] Date of Patent: Apr. 7, 1998

[54] CRAPE MYRTLE SHRUB NAMED 'WHIT III'

[76] Inventor: Carl E. Whitcomb, P.O. Box 2383, Stillwater, Okla. 74076

[21] Appl. No.: 744,408

[22] Filed: Nov. 7, 1996

[51] Int. Cl.[6] ..... A01H 5/00

[52] U.S. Cl. ..... Plt./67.3

[58] Field of Search ..... Plt./67.3

[56] References Cited

U.S. PATENT DOCUMENTS

| | | | |
|---|---|---|---|
| P.P. 4,182 | 1/1978 | Chopin | Plt./54 |
| P.P. 4,183 | 1/1978 | Chopin | Plt./54 |
| P.P. 4,184 | 1/1978 | Chopin | Plt./54 |
| P.P. 4,185 | 1/1978 | Chopin | Plt./54 |
| P.P. 5,302 | 10/1984 | Chopin | Plt./54 |
| P.P. 6,365 | 11/1988 | Whitcomb | Plt./54 |

*Primary Examiner*—James R. Feyrer
*Assistant Examiner*—Elizabeth C. Kemmerer
*Attorney, Agent, or Firm*—Bill D. McCarthy; Phillip L. Free, Jr.; Randall K. McCarthy

[57] ABSTRACT

A new and distinct variety of crape myrtle, *Lagerstroemia indica*, which is characterized by a dense shrub form that may reach eight to ten feet in height, leathery leaves which emerge ruby red and slowly change to purplish green, early and long flowering season that continues after seed head production, inflorescences which are six to twelve inches tall and four to eight inches wide, and flower petals that range from bright red-purple on hot summer days to less intense color on cooler or cloudy days.

2 Drawing Sheets

BACKGROUND OF THE INVENTION

1. Field of the Invention

The present invention relates to a new and distinct variety of cultivar of the ornamental shrub, *Lagerstroemia indica*, commonly known as crape myrtle.

2. Description of the Prior Art

The crape myrtle shrub is native to eastern China and was introduced into North America in the late 1700s. Since then, this popular ornamental shrub has been grown extensively throughout the continent. Over the years, seedlings and hybrids between *L. indicia* and *L. fauriei*, have been selected for various growth forms, flower colors, or other features and propagated asexually. An assortment of methods have been utilized in attempting to develop improved varieties of crape myrtles, at least several of which have had U.S. Plant patents issued.

For example, U.S. Plant Pat. No. 4,182, U.S. Plant Pat. No. 4,183, U.S. Plant Pat. No. 4,184 and U.S. Plant Pat. No. 4,185 disclose and claim a series of four new varieties of *Lagerstroemia indicia* produced by crossing previously known varieties. Each of these new varieties was characterized as having a weeping growth habit at maturity, U.S. Plant Pat. No. 5,302 also discloses a new variety of crape myrtle exhibiting a weeping growth habit at maturity.

U.S. Plant Pat. No. 6,365 discloses a variety of crape myrtle derived from seedlings that had been treated with a mutation inducing chemical. The plant was characterized as having variegated pink flowers bordered by pure white and flowering over an extremely long period of time.

It is generally known that ethylmethane sulfonic acid methyl ester, EMS, is capable of producing plant mutations. EMS sometimes induces partial or complete sterility in the mutant plant and the mutants often have thicker than normal leaves and variegated flowers, with an occasional flower that is a solid color among the predominantly variegated flowers. The new variety of crape myrtle of the present may be such a mutant.

SUMMARY OF THE INVENTION

The present invention involves the discovery of a new and distinct variety of crape myrtle, *Lagerstroemia indicia*, which has been given the cultivar name "Whit III" and which is characterized by a dense shrub form that may reach eight to ten feet in height. The leaves of the plant are more leathery than the species average, emerging ruby red and slowly changing to purplish green, then to dark green. Inflorescences are six to twelve inches tall and four to eight inches wide. Individual petals are a bright red-purple. During hot summer days the flowers are more intense in color, whereas on cooler, overcast days the flowers are less intense in color. Flowering generally begins early in the season relative to other crape myrtle varieties, e.g., early July in north central Oklahoma, but flowering continues until frost. Flowering continues even after seed heads are produced. By contrast, many varieties of crape myrtle plants bloom heavily in July or August, set a heavy seed crop and flower sparingly, if at all, for the rest of the growing season.

BRIEF DESCRIPTION OF THE DRAWINGS

FIG. 1 is a photographic view of my new crape myrtle shrub in full color showing the general form and arrangement of a typical plant.

FIG. 2 is a photographic view in full color of the new and maturing foliage of the shrub of FIG. 1, showing the new growth and the progression of color change as the leaves age.

FIG. 3 is a photographic view in full color of flowers and flower buds of the shrub in FIG. 1.

DESCRIPTION OF THE VARIETY

The new variety of crape myrtle, which has been given the cultivar name "Whit III," was selected from over 65,000 seedlings grown from a seedling parent that had been selected because of the dark foliage and near red flowers and produced large quantities of seeds with good germination and seedling vigor. Prior to planting, the seeds were treated with ethylmethane sulfonic acid methyl ester, EMS, which is generally known to be capable of producing plant mutations. Treated seeds were plants in flats in the greenhouse. After the seeds germinated, the seedlings were transplanted into small containers and mildew was introduced from susceptible seedlings in large containers. Seedlings susceptible to mildew or with poor vigor were rogued out and the remainder of the seedlings were planted in rows in an open field for further evaluation. The new variety was selected from the population in the field for the unique foliage color, growth form, and flower color. It may be a mutant arising from the EMS treatment, however, it does not have bicolor flowers or sterility which are common among mutants.

Softwood cuttings taken from the original parent have been successfully rooted in a medium of peat and perlite under intermittent mist in Oklahoma. Subsequent cuttings taken from plants resulting from previous cuttings have been similarly rooted. Growth, flowering, and flower and foliage color remain consistent with the parent. The plant does not reproduce true from seed.

In one test, fifteen plants of the new variety, approximately twelve to sixteen inches tall, were planted in late July in an open field in north central Oklahoma. The plants were watered once, then evaluated for drought tolerance and the ability to establish in adverse conditions. Thirteen of the fifteen plants survived. By contrast, other varieties of crape myrtle selections of similar age were treated similarly and most or all died.

A detailed description of the new variety of crape myrtle follows:

Parentage: Selected from over 65,000 crape myrtle seedlings grown from a selected seedling parent. The seeds were treated with EMS to induce mutations. The thick leathery leaves are the only indication that the new variety may be a mutant.

Growth: Vegetative growth is rapid in spring and continues until early July when flowering begins. Only modest growth occurs after flowering begins. Several vertical stems are typically produced, having similar vigor and many side branches, thus creating the dense shrub form shown in FIG. 1. Height may reach eight to ten feet with age.

Foliage: Leaves are similar in size to the species average, but are more thick and leathery and with excellent retention even during severe drought. New leaves emerge ruby red (FIG. 2), Red-purple Group 59-A and CIE coordinates 0.455, 0.282, 5.6 (color notations from The Royal Horticulture Society Colour Chart, 1966 and the Commission International de l'Eclairage Society 1931) and gradually change to purplish-green, then to arras green, Green Group 139-A (R.H.S.) and CIE 0.292, 0.400, 6.4. The color varies with light intensity and growing conditions. Foliage has been very resistant to powdery mildew in Oklahoma.

Flowers: Individual petals are red-purple in full sun (FIG. 3) Red-purple group 61-B (R.H.S.) and CIE 0.448, 0.248, 7.7. Flowers produced during overcast periods are more subdued in color. As flowers age, they generally fall cleanly from the inflorescence without discoloring or becoming unattracive. Unopened flower buds are ruby red, Red-purple Group 59-A (R.H.S.) and CIE 0.455, 0.282, 5.6 and nearly identical to the color of the new foliage. The new variety generally begins flowering in early July and continues into October in Oklahoma. This period is longer than most seedlings and cultivars of other crape myrtle varieties. Flowering continues during drought or periods of prolonged heat. Flowering continues even after seed pods and seeds are formed.

Cold hardiness: The new variety of crape myrtle has withstood temperatures of −5° F., 2° F. and 0° F. with no injury. The top of the plant was killed to the soil line at −13° F., but quickly regrew the following spring and flowers in summer.

I claim:

1. A new and distinct variety of *Lagerstroemia indica*, crape myrtle plant substantially as shown and described and partially characterized by a dense shrub form that may reach eight to ten feet in height, ruby red new leathery foliage that slowly changes to purplish-green then with age to dark green, ruby red flower buds, red-purple flowers, many seeds, yet an exceptionally long bloom period.

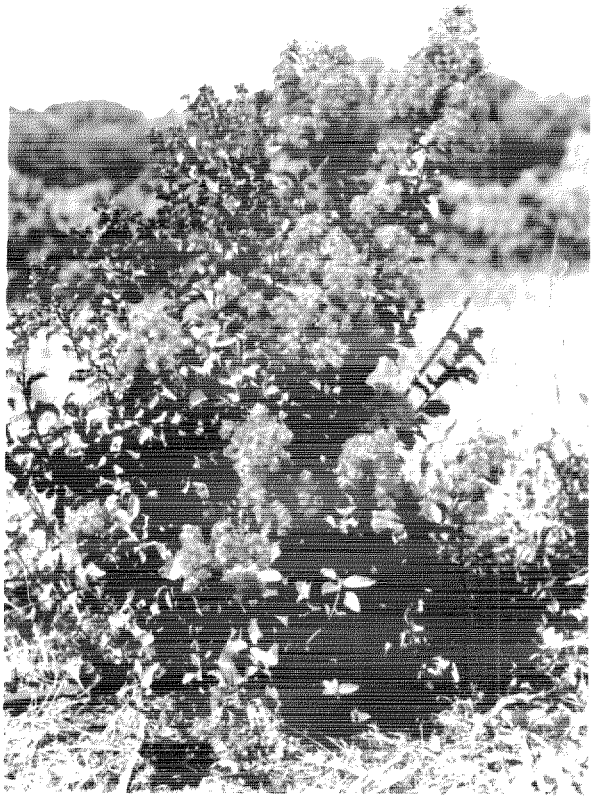

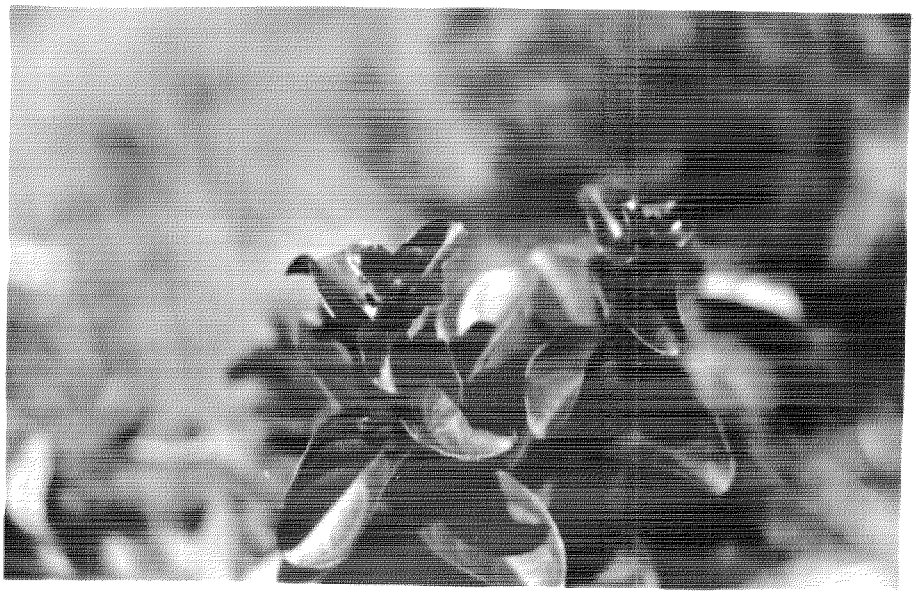
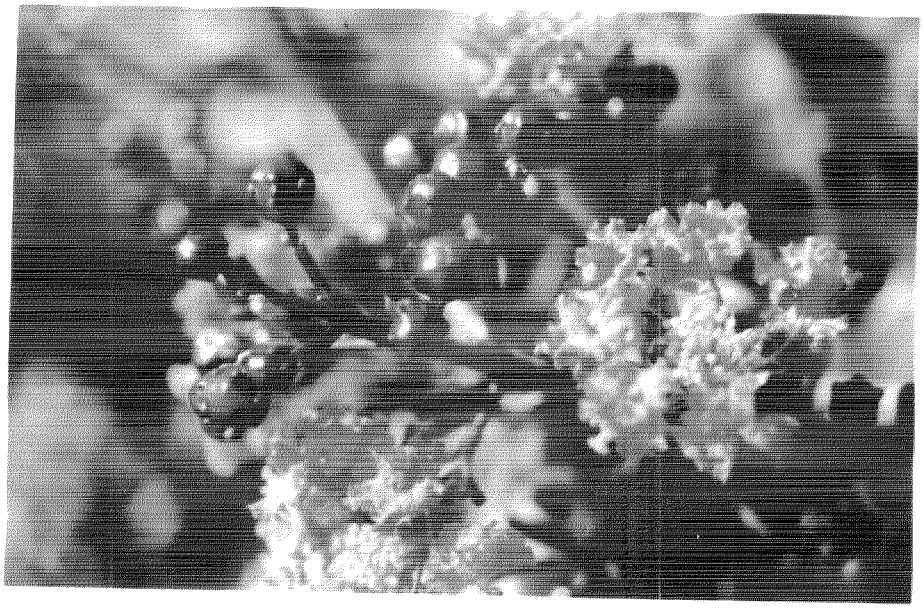

* * * * *